United States Patent
Gobbi et al.

(10) Patent No.: US 9,668,673 B2
(45) Date of Patent: Jun. 6, 2017

(54) SYSTEM FOR THE AUTOMATIC DETECTION OF RESPIRATORY DISEASES AND FOR THE PREDICTION OF FUTURE ACUTE AIRWAY INSTABILITIES

(75) Inventors: Alessandro Gobbi, Turano Lodigiano (IT); Pasquale Pio Pompilio, Milan (IT); Raffaele Dellaca', Como (IT); Antonio Pedotti, Milan (IT)

(73) Assignee: POLITECNICO DI MILANO, Milan (MI) (IT)

( * ) Notice: Subject to any disclaimer, the term of this patent is extended or adjusted under 35 U.S.C. 154(b) by 849 days.

(21) Appl. No.: 13/822,098

(22) PCT Filed: Sep. 9, 2011

(86) PCT No.: PCT/IB2011/002103
§ 371 (c)(1),
(2), (4) Date: Mar. 12, 2013

(87) PCT Pub. No.: WO2012/032402
PCT Pub. Date: Mar. 15, 2012

(65) Prior Publication Data
US 2013/0165807 A1  Jun. 27, 2013

(30) Foreign Application Priority Data
Sep. 10, 2010  (IT) .............................. BG2010A0049

(51) Int. Cl.
*A61B 5/02*     (2006.01)
*A61B 5/085*    (2006.01)
(Continued)

(52) U.S. Cl.
CPC .............. *A61B 5/085* (2013.01); *A61B 5/087* (2013.01); *A61B 5/7275* (2013.01); *A61B 5/4842* (2013.01)

(58) Field of Classification Search
CPC ...................................................... A61B 5/085
See application file for complete search history.

(56) References Cited

FOREIGN PATENT DOCUMENTS

WO     2005104944 A1    11/2005

OTHER PUBLICATIONS

"Specific Airway Resistance, Interrupter Resistance, and Respiratory Impedance in Healthy Children Aged 2-7 Years" by Klug et al., Pediatric Pulmonology 25, pp. 322-331, 1998.*

(Continued)

*Primary Examiner* — Patricia Mallari
*Assistant Examiner* — Vasuda Ramachandran
(74) *Attorney, Agent, or Firm* — King & Schickli, PLLC

(57) ABSTRACT

A system for automatically predicting acute airway events in patients, comprising: a device for measuring the respiratory impedance of a human subject during a plurality of respiratory cycles of said human subject; said respiratory impedance comprising a real part and an imaginary part; said device measuring said respiratory impedance two times per day to provide a plurality of measurements; means for calculating the relative variation of said plurality of measurements; means for evaluating the probability of respiratory pathology presence in the subject under examination when the value of the imaginary part of said impedance is greater than 35%; means for predicting a relapse in the patent under examination within an established future time window, once the presence of the pathology has been ascertained, if the variation coefficient of the real part of said impedance is greater than 0.4.

4 Claims, 4 Drawing Sheets

(51) Int. Cl.
    *A61B 5/00* (2006.01)
    *A61B 5/087* (2006.01)

(56) References Cited

OTHER PUBLICATIONS

"Home monitoring of within-breath respiratory mechanics by a simple and automatic forced oscillation technique device" by Dellaca et al., IOP Publishing, V. 31, No. 4, Apr. 2010.*

Urs Frey; Tanja Brodbeck; Arnab Majumdar; Robin Taylor D; Ian Town G; Michael Silverman; Béla Suki Risk of severe asthma episodes predicted from fluctuation analysis of airway function Nature: international weekly journal of science, Dec. 1, 2005 Nature Publishing Group, United Kingdom—ISSN 0028-0836 vol. 438, Nr:7068, pp. 667-670.

Gobbi A; Milesi I; Govoni L; Pedotti A; Dellaca R L A new telemedicine system for the home monitoring of lung function in patients with obstructive respiratory diseases eHealth, Telemedicine, and Social Medicine, 2009. eTELEMED '09. International Conference on, Feb. 1, 2009; Feb. 1, 2009-Feb. 7, 2009 IEEE, Piscataway, NJ, USA—ISBN 978-1-4244-3360-5 ; ISBN 1-4244-3360-6 pp. 117-122.

Dellaca R L; et al Home monitoring of within-breath respiratory mechanics by a simple and automatic forced oscillation technique device Physiological Measurement, Nov. 17, 2011 Institute of Physics Publishing, Bristol, GB—ISSN 0967-3334 vol. 31, Nr:4, pp. N11-N24.

Gobbi A; et al Long-term temporal fluctuations of respiratory resistance in asthma Annual Congress. European Respiratory Society ERS. Abstracts, Sep. 21, 2010 XX, XX p. 1.

\* cited by examiner

SYSTEM FOR THE AUTOMATIC DETECTION OF RESPIRATORY DISEASES AND FOR THE PREDICTION OF FUTURE ACUTE AIRWAY INSTABILITIES

The present invention relates to a system for automatically predicting acute airway events (relapses) in patients suffering from respiratory pathologies, and to a relative method.

Many respiratory pathologies, such as asthma and chronic obstructive bronchopneumopathy (BPCO), are chronic inflammatory diseases characterised by extremely variable recurrent symptoms, such as expiratory flow limitation, which affect millions of children and adults throughout the entire world. It is in fact estimated that 300 million people suffer from asthma (GINA, 2009 guidelines) and 80 million suffer from BPCO (WHO, 2006). Their diagnosis is based mainly on clinical tests for their episodic symptoms; however their extreme variability would require continuous monitoring of at least once every day. In addition, respiratory patents often suffer from acute respiratory crises (relapses) which, in the most serious cases and in the most advanced stages of the pathology, often involve hospital recovery and a considerable worsening of their quality of life. Domiciliary monitoring devices offer a possible solution to the need to periodically record with adequate rapidity the respiratory parameters of interest and their physiological and pathological time fluctuations. However, in clinical practice, the evaluation and treatment of asthma and BPCO still depend on tests using spirometers or peak flow measurers, which do not provide data corresponding to the quality requirements of international guidelines if the measurements are made without supervision by trained personnel (doctors, technicians, nurses, etc.) (Allen 2003, Brouwer 2006). Moreover, the results of these tests mainly reflect the size of the large airways, while undervaluing the extent of airflow limitation present in the peripheral airways (Pride 1985).

The object of the present invention is to provide a system and method for predicting relapses by continuously monitoring respiratory parameters.

This and further objects are attained according to the present invention by a system and method for predicting acute respiratory events, in accordance with the accompanying claims.

The present invention provides a method for predicting future airway instabilities and worsening of the patient's state of health. It is based on a device which implements the forced oscillation technique (FOT), which has proved more suitable than spirometry in measuring specific respiratory parameters at the patient's domicile, without supervision by trained personnel (Dellaca' 2010). As an instrument for investigating respiratory physiopathology, FOT is a non-invasive versatile method requiring minimum collaboration by the patient during the measurement (Oostveen 2003). During a typical FOT test, the patient has merely to breathe spontaneously through the device nozzle while the device stimulates the respiratory system with a single or multiple frequency pressure stimulus and simultaneously records the pressure signals and the air flow through the patient's mouth. The overall ratio between these two signals is an estimate of the input impedance of the respiratory system, usually indicated by Zrs, which itself can be divided into its real part (resistance, Rrs) and its imaginary part (reactance, Xrs). The method of minimum squares described in Horowitz et al. (1983) provides an intra-respiratory estimate of Zrs, and hence of Rrs and Xrs, during the FOT test.

These colleagues (2001) measured Zrs using a standard clinical FOT device for a maximum time of 15 minutes and sought differences in the logonormal Zrs and Rrs values within a population of normal and asthmatic subjects. They maintained that it was possible to use short term variability (expressed as standard deviation) of the airway resistance as a disease indicator.

Short term variability analysis is also the subject of a patent (WO 2005/104944) in which the inventors applied FOT to a group of about 40 asthmatic children and 30 controls of the same age, for a total of 180 seconds per test, before and after administering a bronchodilator drug (BD). They estimated the Zrs value using a Fourier method, to obtain 180 Zrs points for each test at each frequency stimulus (range 4-34 Hz). They calculated the Rrs standard deviation (SDRrs), the average Rrs and the average Xrs, and found significant differences between healthy and asthmatic patients under basic conditions only at 4 Hz. In addition, the bronchodilator drug BD significantly reduced the SDRrs. They concluded that the analysis of this 180 second Rrs variability could be an instrument for non-invasive diagnosis of asthma, and that Rrs and Xrs analysis before and after BD could be useful in understanding the activity of the airway smooth musculature, which is commonly considered to be involved in asthma pathophysiology.

However, their conclusions were not confirmed in subsequent studies (Diba, 2007 and Muskulus, 2010) in which the authors sought to reproduce the same experiments and to measure the same quantities, but without finding the same results.

The contradictory results obtained from the aforesaid studies are associated with the fact that the "short term variability" of Rrs and Xrs can be influenced by numerous noise sources, including: a) the natural variability of Rrs and Xrs over a short time period (Randell 1999), b) the natural end-of-expiration volume fluctuations, c) the non-linearities which occur during normal respiration within each breath, and d) respiratory parameter fluctuation between inspiration and expiration (Goldman 2002).

These problems can be resolved by concentrating the analysis only on the inspiratory part of Rrs and Xrs (Rinsp and Xinsp respectively), which is more stable than the expiratory or total part (Kubota 2009), and averaging the Rinsp and Xinsp intra-respiratory values over the entire test. Hence for each test an average Rinsp value and an average Xinsp value can be derived.

On this basis, the present invention develops a system and automatic method for predicting future relapses in patients suffering from respiratory pathologies.

Further characteristics and advantages of the present invention will be more apparent from the description of a preferred but non-exclusive embodiment according to the invention, illustrated by way of non-limiting example in the accompanying drawings, in which.

Figure 1:
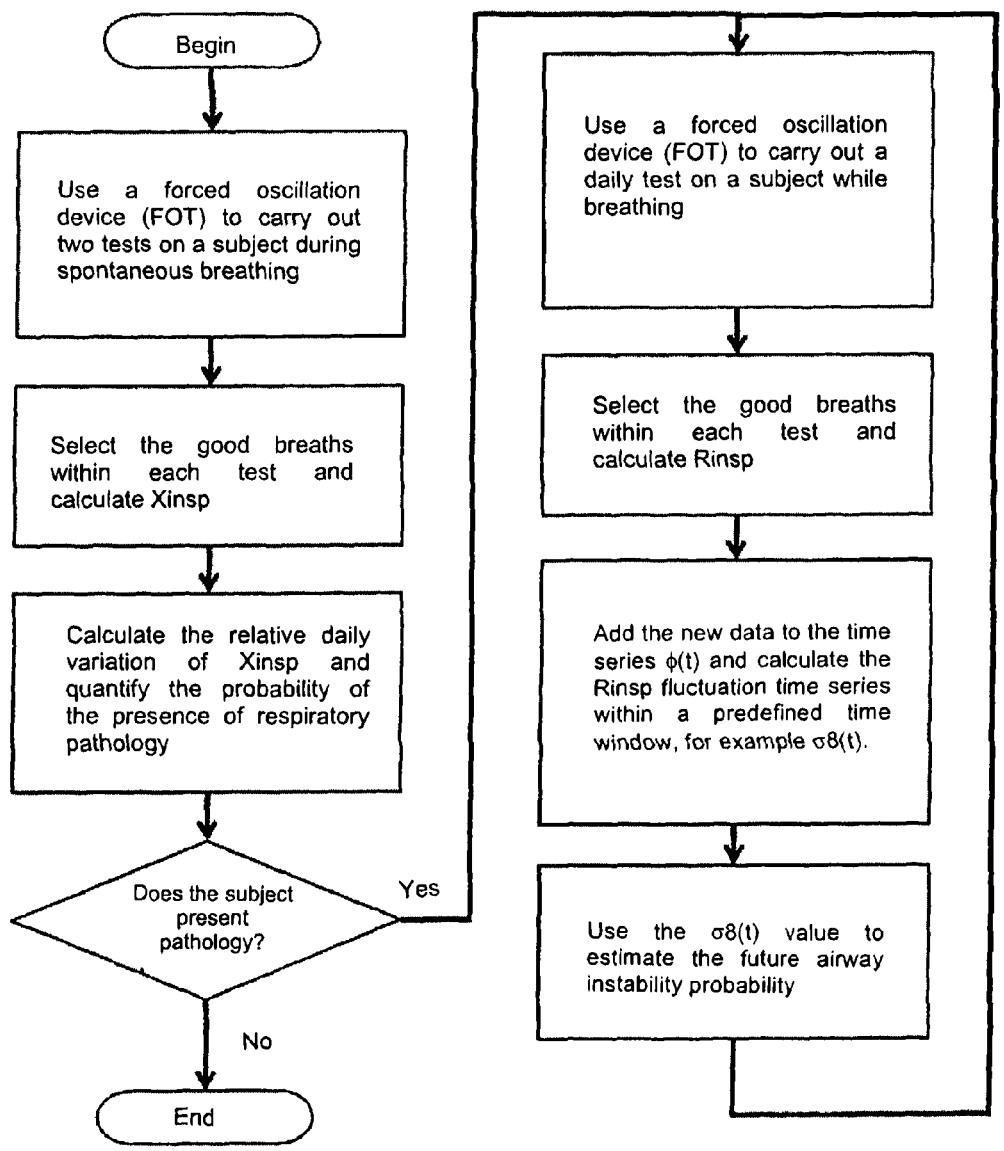
FIG. 1 is a flow diagram for early identification of acute events.

With reference to the flow diagram of FIG. 1, the invention uses a device able, while breathing, to measure mechanical respiratory parameters (Rrs and Xrs) during a test in which the respiratory system is examined with a pressure stimulus containing a single frequency or a plurality of sinusoidal signals (FOT). Technical details, the precision, stability and reliability of a suitable but non-exclusive device are described in Dellaca' et al. (2010). During the test the subject is required to wear a nose peg, and to support the cheeks with the hands, while breathing spontaneously through the device nozzle (for two minutes in this example).

The invention uses a method for calculating the average respiratory parameters in each test but selecting only those breaths which are not influenced by unnatural effects such as cough, closure of the glottis, swallowing, etc. For this purpose, the automatic algorithm described in Gobbi et al. (2009) can be used. Alternatively, other manual, automatic or semi-automatic techniques can be used to calculate the Zrs from the recorded pressure and flow signal.

Figure 2:
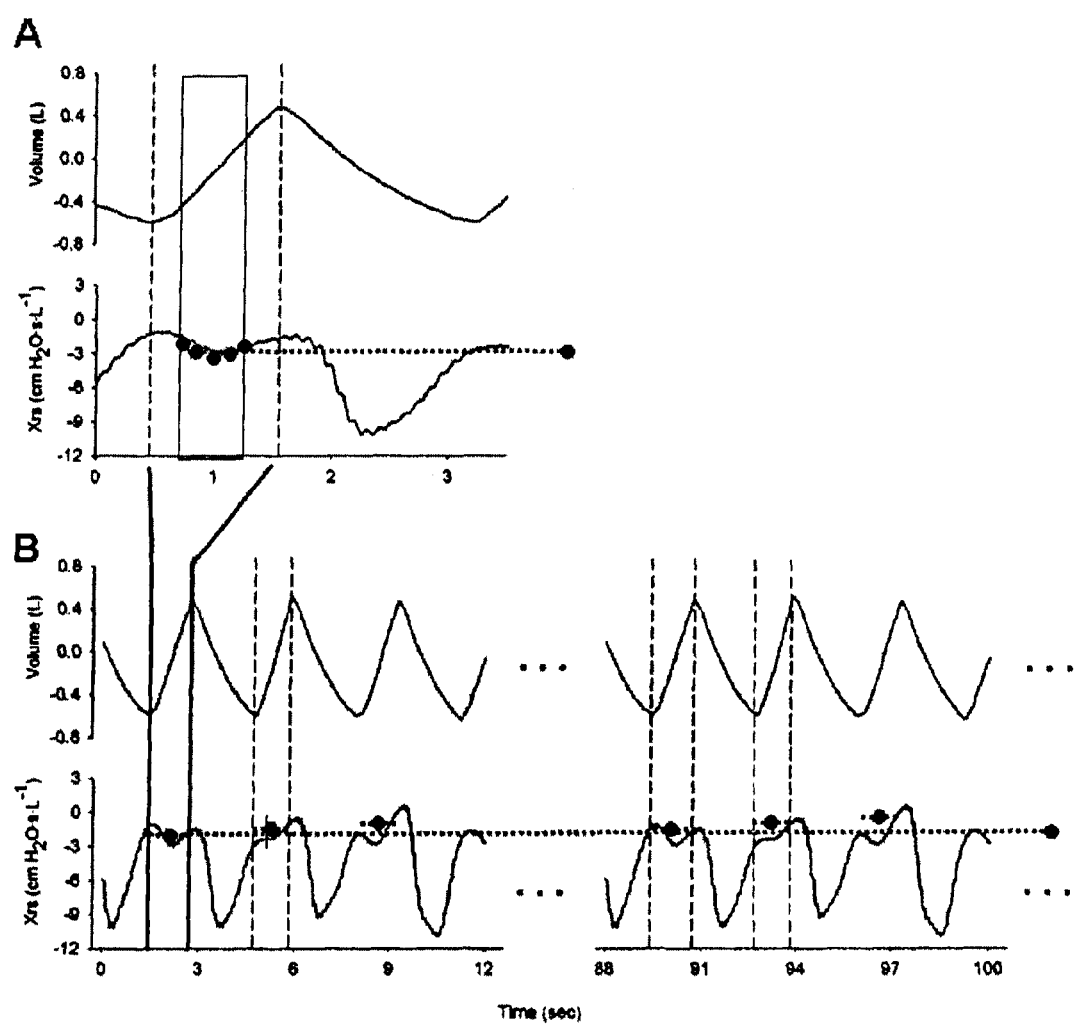
FIG. 2A is a detail of FIG. 2B, representing the method for calculating the average value of a respiratory parameter (Xinsp) within a given test.
FIG. 2B represents the method for calculating the average value of a respiratory parameter (Xinsp) within a given test.

The average Zrs of each (good) breath within a given FOT test is then calculated. The analysis of the present invention is then carried out in inspiration and/or in expiration separately, with the inspiratory phase preferable. As an example for the ensuing description, we have used two inspiratory parameters derived from the Zrs: the average inspiratory resistance (Rinsp) and the average inspiratory reactance (Xinsp), defined as the average value of Rrs and Xrs during inspiration in the overall test. FIG. 2 shows how to calculate Xinsp, measured in $cmH_2O \cdot s \cdot L^{-1}$. In the example shown in FIG. 2A, those Xrs points (shown here as a function of time) lying within the central ⅗ of the inspiration are selected (automatically or manually) and the average value is calculated. This quantity represents the average reactance value during inspiration of the $i^{th}$ breath. This procedure is reiterated on all good breaths of a given test (FIG. 2B), the average of all these points (FIG. 2B) constituting the Xinsp parameter of the FOT test under examination. FIG. 2 also shows the current volume, measured in L, with respect to time, to correctly identify the central $⅗^{th}$ of each inspiration and then to eliminate the inspiration end and expiration end points of each breath from the parameter average value calculation.

The object of this operation is to remove parameter non-linearities close to the zero flow points (inspiration end and expiration end). In this example, the pressure and flow signals were sampled at 200 Hz, the Xinsp being estimated using windows of 40 data points, each superimposed by 10 points (25%) on the preceding.

Consequently, the time series of a given FOT parameter (eg. Xinsp) is the sequence of average values of the same parameters calculated within each test.

The invention comprises two distinct steps:
 1. identifying the presence of the respiratory pathology by measuring the relative daily variability of Xinsp
 2. early identification of future respiratory crises and/or abnormal Rinsp variations by continuous daily FOT measurements for at least 4 days, with relative quantification of average Rinsp fluctuations.

With regard to point 1, the tests must be carried out twice in the same day, preferably morning and evening. The relative daily variability can be quantified, for example, as the difference between the morning value and the evening value:

$$\Delta P_\% = \frac{P_1 - P_2}{P_2} \cdot 100 \qquad [1]$$

where P is the respiratory parameter and $P_1$, $P_2$, indicate in this example the morning and evening value of P. For example, the parameter P could be Xinsp.

This system quantifies the presence of the respiratory pathology in a given subject starting from a probability density estimation of the relative variability (equation [1]). The kernel smoothing technique (Rosenblatt, 1956) can be used to calculate this probability density, and the Bayes theorem to invert this estimation and to quantify the probability of having the disease.

Figure 3:
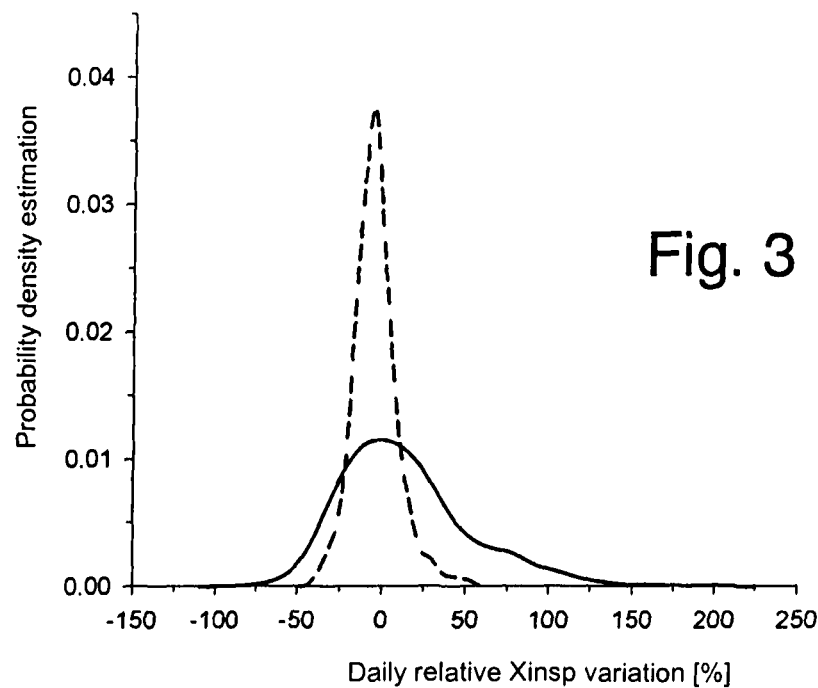
FIG. 3 shows the probability density estimation of the daily variability of Xinsp measured at 5 Hz, taken as an example.

By way of example, we compared the variability density estimations in a population of 10 normal subjects and 10 asthmatic individuals who recorded their Zrs values daily, twice a day, for at least 6 months (FIG. 3). This figure shows the relative daily variability density estimations (equation [1]) of Xinsp, for the control group (dashed lines), and for the asthmatic group (continuous lines). From a qualitative viewpoint, the variability of the asthmatic group is much higher than that observed in the control group. From a quantitative viewpoint, there are significant differences between the average value (p<0.01) and the standard deviation (p<0.001) of the daily relative variability in Xinsp between the controls and the asthmatic subjects.

Figure 4:
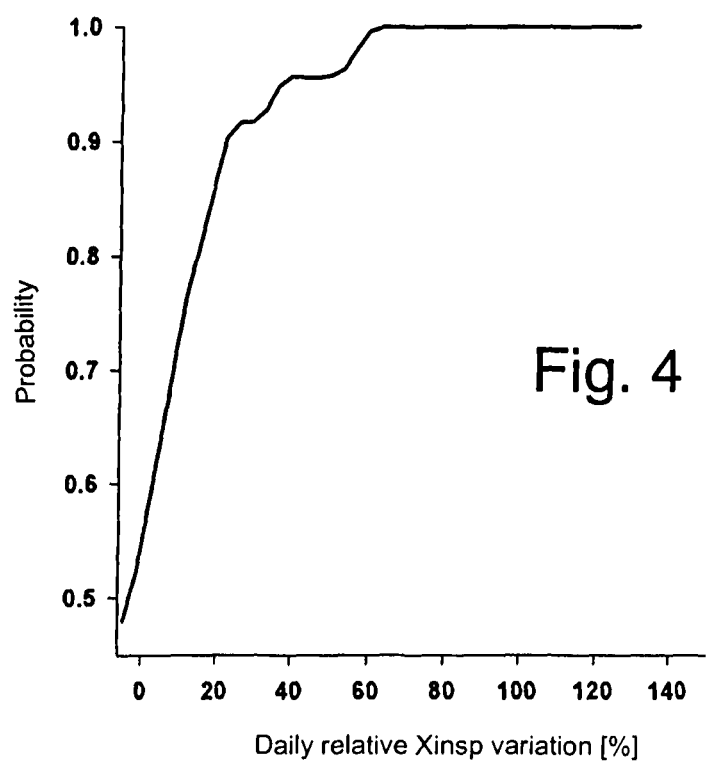
FIG. 4 shows a probability of being asthmatic given the relative daily variation of Xinsp.

Starting from the probability density estimations shown in FIG. 3 and using the Bayes formula, the curve shown in FIG. 4 is obtained which quantifies, in probabilistic terms, the possibility of having the respiratory pathology based on the relative daily variability of Xinsp, measured in accordance with the equation [1] and shown on the horizontal axis in FIG. 4; from this figure it can be seen that a relative daily variation of Xinsp>40%<50% is associated with a 95% probability of having the respiratory disease.

If the daily variation of Xinsp is 10%, the probability is about 0.6 (60%), if 20% the probability is about 75%, if 40% the probability is >95%. For example, it can be considered that the respiratory pathology is present when the value of Xinsp is greater than 35%. Having ascertained the presence of the respiratory pathology in a given subject, abnormal fluctuations of the respiratory parameters and/or future acute respiratory crises (relapses) can be predicted by continuous daily monitoring for at least 4 consecutive days using the FOT technique.

This system hence quantifies the risk of future extreme events (airway instability), given a current average variability value of a respiratory parameter measured for at least 4 consecutive days.

As an example, the conditional probability of having an extreme value in the middle of the next week, in one week or in two weeks given a current Rinsp variability quantity is described hereinafter and shown graphically in FIG. 5.

An extreme value ($\phi_{crit}$) of the time series $\phi(t)$ of a respiratory parameter (constructed from the observations described for FIG. 2) is defined as a value greater than a certain threshold. In this example the threshold was fixed equal to double the value predicted from the Pasker equation (Pasker 1994), according to the age, sex, weight and height of a given subject. For each of the 20 subjects described for FIG. 3 and monitored at home by FOT for at least six months, we calculated:

the time series φ(t) of Rinsp (average value of FOT test, calculated in the same manner as the Xinsp value in FIG. 2) for each subject, separately for morning and evening, as previously described;

the time series φ(t) of the average Rinsp variability in time windows comprising 2, 4 and 8 consecutive tests, for each subject. Each point of these new time series is calculated by taking a group of data of the original time series φ(t) equal to the length of the time scale (2, 4 or 8 consecutive days respectively) and calculating the average Rinsp fluctuation in that window. In our example, this average fluctuation was quantified by the variation coefficient, given by the ratio of standard Rinsp deviation to its average value. The group is then moved forward by one point (i.e. one FOT test) and the procedure is repeated. The new time series obtained are indicated as $\sigma_2(t)$, $\sigma_4(t)$, and $\sigma_8(t)$. The conditional probability π which verifies an extreme event within a time window τ in φ(t) (shown on the ordinates of FIGS. 5A and 5B), considering the current value of $\sigma_2(t)$, $\sigma_4(t)$, and $\sigma_8(t)$, can be calculated as follows: an arbitrary fixed number of ranges η is firstly chosen (10 in this example) into which the range of $\sigma_2(t)$, $\sigma_4(t)$, or $\sigma_8(t)$ is subdivided. As each point of $\sigma_2(t)$, $\sigma_4(t)$, or $\sigma_8(t)$ constitutes an average fluctuation measurement in the considered time window, it already determines the range η within which this measurement will fall; the total number of measurements within this range N(η) is incremented by one unit, and a separate counter Ny(η) being incremented if each φ(t) value within the window τ moved forward respectively by 2, 4 or 8 days is above $\phi_{crit}$. The π(η) is then obtained by using the Bayes theorem, on the assumption that the probability that an extreme event $\pi(\eta, p_y)$ occurs is distributed uniformly between 0 and 1, $p_y$ being the true (and unknown) probability.

When N and Ny are sufficiently large, this probability can be estimated as the frequency Ny(η)/N(η), as described for example in Frey et al. (2005).

Figure 5:
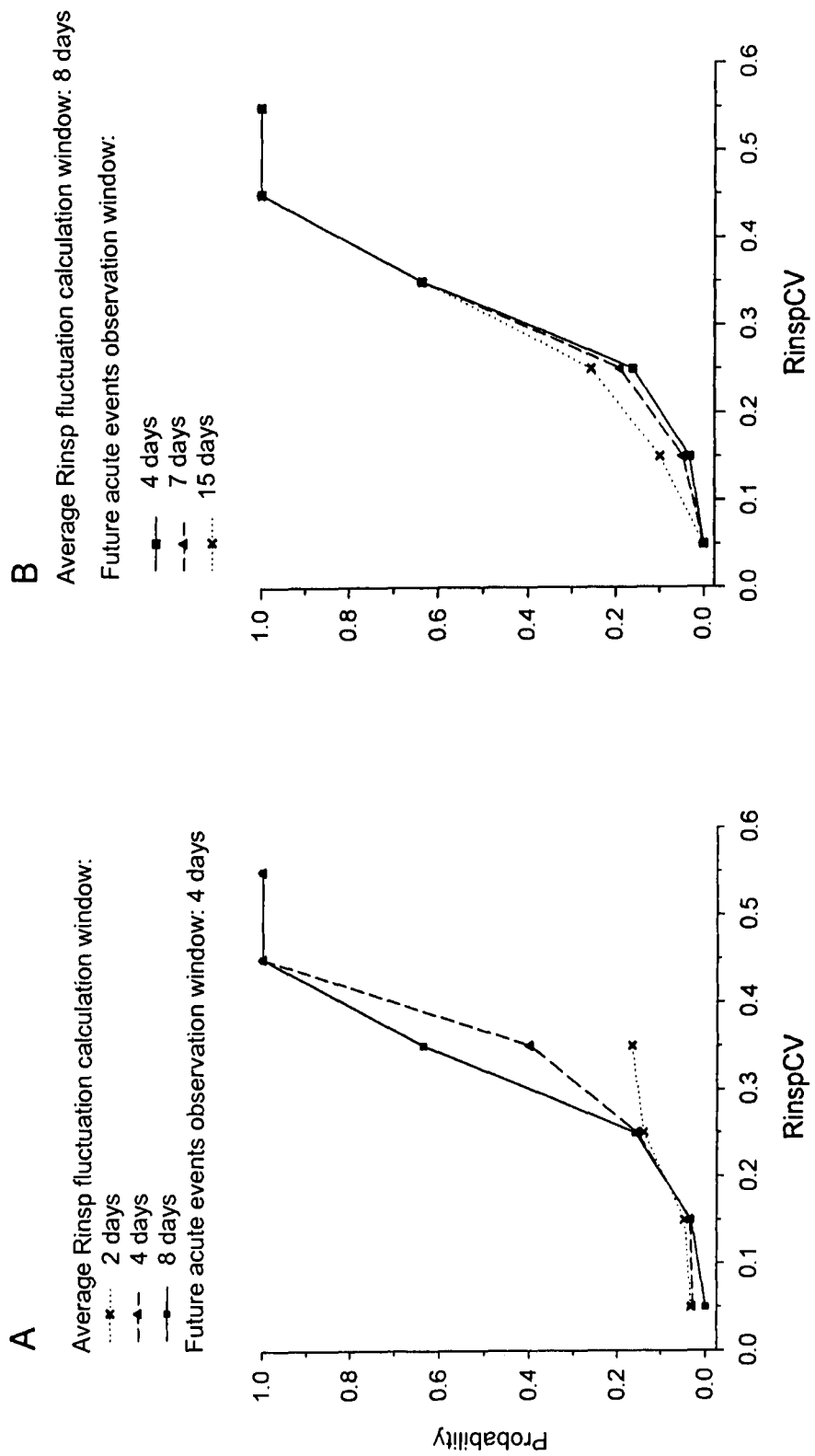
FIG. 5A shows the conditional probability of having a future extreme event in the next half week (4 days), given the average fluctuation of Rinsp calculated on 2, 4 or 8 consecutive tests.
FIG. 5B shows the conditional probability of having a future extreme event in the next half week (4 days), next week (7 days) and next two weeks (15 days), given the average fluctuation of Rinsp observed in the last 8 days.

FIG. 5 shows some predictors of future extreme events calculated using the data of the previous 10 asthmatic subjects and 10 normal subjects.

In particular, FIG. 5A shows the conditional probability on the individual basis of having a future Rinsp extreme event within a future prediction window of a half week, as a function of the average Rinsp fluctuation, expressed in this example as the coefficient of variation (CV) and calculated within the last 2 days, 4 days and 8 days. Each predictor point is the average probability within a RinspCV range centred on that point with a half-amplitude of 0.05. In FIG. 5A the prediction window is set at a half week and the predictors constructed by $\sigma_2(t)$, $\sigma_4(t)$, or $\sigma_8(t)$ are compared. The minimum observation time scale necessary to identify with high probability the risk of extreme events is 4 days. However, the form of the predictor σ=f(CV) approaches a more ideal behaviour (i.e. a step function with probability 0 below a given value of CV and probability 1 above it) when the average Rinsp fluctuation is calculated over 8 days.

In contrast, FIG. 5B shows the conditional probability on the individual basis of having a future Rinsp extreme event or relapse within a future prediction window of a half week, one week and two weeks, as a function of the average Rinsp fluctuation calculated over 8 days. As in FIG. 5A, each predictor point represents the average probability that an acute event occurs within a range centred on that point with a half-amplitude of 0.05. For intermediate Rinsp fluctuation values over 8 days (i.e. of the RinspCV shown as ordinate), the risk of extreme Rrs values increases with the observer's horizon (i.e. passing from a half week to two weeks); however, for higher values the predictors merge, suggesting that a high instability in airway calibre usually precedes the extreme event by a very few days.

In the example shown in FIG. 5B, if the measured RinspCV is 0.35, the probability of having a future extreme event is about 60%; at a value of 0.4, the probability is about 80%; at a value of 0.45, the probability is about 100%.

In both the cases shown in FIGS. 5A and 5B it can be assumed that there is a good probability of having an extreme event if the RinspCV is greater than 0.4.

Implementation of the system for automatically predicting acute airway events in patients with respiratory pathologies, according to the present invention, is achieved by means of a suitably programmed computer, which receives as input the measurements made on the patient, calculates the impedance values and automatically calculates the presence of the respiratory pathology, then if positive it calculates the probability of future respiratory crises. Specifically, with reference to FIG. 1, a forced oscillation device (FOT) is used to carry out two tests on a subject during spontaneous breathing, preferably morning and evening.

The good breaths are selected within each measurement and Xinsp is calculated.

The relative daily variation of Xinsp is calculated and the probability of the presence of the respiratory pathology is quantified, for example if the value of Xinsp is greater than 35%.

If the subject does not present the pathology or the value of Xinsp is less than 35%, the procedure terminates.

Otherwise, again using the forced oscillation device (FOT), continuous daily monitoring is carried out on the patient.

The good responses are selected within each measurement and Rinsp is calculated.

The new data are added to the time series F[t] and the Rinsp fluctuation time series is calculated within a predefined time window, for example σ8[t].

The σ8[t] value is used to estimate the future airway instability probability by calculating the Rinsp variation coefficient (CV) for example during the last 4 days, and if this value is greater than 0.4 there is good probability (equal to or greater than 80%) that an extreme event or a relapse of the patient will occur in the future.

The invention claimed is:

1. A method of automatically predicting acute airway events in respiratory patients having asthma or chronic obstructive bronchopneumopathy (BPCO), comprising the steps of measuring the respiratory impedance of a human subject by a forced oscillation technique device during a plurality of respiratory cycles of said human subject where said respiratory impedance comprises a real part and an imaginary part; said step of measuring the respiratory impedance taking place two times per day to provide a plurality of measurements; calculating, using a suitably programmed computer, a relative variation of said imaginary part of said plurality of measurements characterized in that said relative variation of said imaginary part, is calculated in accordance with the following formula:

$$P_\% = \frac{P_1 - P_2}{P_2} \cdot 100$$

Where P is the respiratory parameter and P1, P2, indicate the value of P calculated from two measurements made at two different moments during the day; evaluating, using the computer, a probability of respiratory pathology presence in the subject under examination when the variation of the imaginary part of said respiratory impedance during inspiration is greater than 35%; calculating, using the computer, over at least 4 days, a coefficient of variation of the real part of said impedance; predicting, using the computer, a relapse of the acute airway event in the patient under examination within an established future time window, once the presence of the pathology has been ascertained, if the coefficient of variation of the real part of said impedance is greater than 0.4; outputting, using the computer, a graphical representation of the predicted relapse.

2. A method as claimed in claim 1 characterized in that said established future time window is 4 or 7 or 15 days.

3. A method as claimed in claim 1 characterized in that said coefficient of variation of the real part of said impedance is given by the ratio between the standard deviation of the real part of said impedance only during inspiration, and its average value.

4. A method of automatically predicting acute airway events in respiratory patients having asthma or chronic obstructive bronchopneumopathy (BPCO), comprising the steps of measuring respiratory impedance of a human subject during a plurality of respiratory cycles of said human subject breathing spontaneously through a device nozzle while an associated device stimulates the human subject's respiratory system with a single or multiple frequency pressure stimulus and simultaneously records pressure signals and air flow through the human subject's mouth, where said respiratory impedance comprises a real part and an imaginary part; said step of measuring the respiratory impedance taking place two times per day to provide a plurality of measurements; calculating, using a suitably programmed computer, a relative variation of said imaginary part of said plurality of measurements characterized in that said relative variation of said imaginary part, is calculated in accordance with the following formula:

$$P_\% = \frac{P_1 - P_2}{P_2} \cdot 100$$

Where P is the respiratory parameter and P1, P2, indicate the value of P calculated from two measurements made at two different moments during the day; evaluating, using the computer, a probability of respiratory pathology presence in the subject, under examination when the variation of the imaginary part of said respiratory impedance during inspiration is greater than 35%; calculating, using the computer, over at least 4 days, a coefficient of variation of the real part of said impedance; predicting, using the computer, a relapse of the acute airway event in the patient under examination within an established future time window, once the presence of the pathology has been ascertained, if the coefficient of variation of the real part of said impedance is greater than 0.4; outputting, using the computer, a graphical representation of the predicted relapse.

* * * * *